United States Patent [19]

Farin et al.

[11] Patent Number: 5,087,257
[45] Date of Patent: Feb. 11, 1992

[54] APPARATUS FOR MONITORING THE APPLICATION OF NEUTRAL ELECTRODES ON A PATIENT UNDERGOING HIGH FREQUENCY ELECTRO-SURGERY

[75] Inventors: Günter Farin, Tübingen; Franz Geiselhart, Reutlingen; Johannes Klett, Ofterdingen, all of Fed. Rep. of Germany

[73] Assignee: Erbe Elektromedizin GmbH, Tubingen, Fed. Rep. of Germany

[21] Appl. No.: 496,885

[22] Filed: Mar. 21, 1990

[30] Foreign Application Priority Data

Apr. 1, 1989 [EP] European Pat. Off. ............ 89105740

[51] Int. Cl.$^5$ ............................................. A61B 17/39
[52] U.S. Cl. ........................................................ 606/35
[58] Field of Search ...................................... 606/35, 32

[56] References Cited

U.S. PATENT DOCUMENTS 3,933,157  1/1976  Bjurwill et al. .................. 606/35
4,657,015  4/1987  Irnich .

FOREIGN PATENT DOCUMENTS 15702124  8/1952  Fed. Rep. of Germany .
3239640   5/1983  Fed. Rep. of Germany .
3544443   6/1987  Fed. Rep. of Germany .
2414812   8/1979  France ............................ 606/35
2516782   5/1983  France .
2146534   4/1985  United Kingdom ............... 606/35

OTHER PUBLICATIONS

European Search Report No. 89 10 5740.

Primary Examiner—Lee S. Cohen
Attorney, Agent, or Firm—Frishauf, Holtz, Goodman & Woodward

[57] ABSTRACT

At least one neutral electrodes insulated from each other is separately connected to the current return terminal of a high frequency electro-surgical equipment are applied in electrical contact with the skin of a patient while surgery is performed with the active electrode of the equipment. A low frequency alternating current is passed through the patient's flesh from one neutral electrode to the other to monitor the quality of contact between the neutral electrodes and the patient. The intensity of the intermeittent high frequency current or a corresponding setting of the high frequency surgery equipment is compared with a signal representative of the monitoring current so that warning signals and/or automatic shut-off of the high frequency equipment will occur when and only when the high frequency current for surgical cutting or coagulation is greater than that which is permissible for the electrical transition conductivity present at the time between the respective neutral electrodes and the skin of the patient without risk of thermal damage to the skin at the place the neutral electrode is applied.

17 Claims, 3 Drawing Sheets

APPARATUS FOR MONITORING THE APPLICATION OF NEUTRAL ELECTRODES ON A PATIENT UNDERGOING HIGH FREQUENCY ELECTRO-SURGERY

FIELD OF THE INVENTION

The invention concerns monitoring the application to a patient of neutral electrode contact surfaces during high frequency surgery in which the surgeon manipulates an active electrode. At least two neutral electrode surfaces, insulated from each other and independently connected to the return current terminal of a high-frequency generator, so that a test or monitoring current can be caused to flow from one neutral electrode surface to another can detect a deficiency in the neutral electrode contact with the patient.

BACKGROUND

Among the known equipment or monitoring the application of the neutral electrodes automatically during high frequency electro-surgery and providing an alarm or a shut-off in certain cases is the equipment disclosed in published German Patent Application PA 15 7021-24 bl of Apr. 2, 1951. In that system upper and lower tolerance limits are set for the resistance interposed between the two neutral counter electrodes, as measured by the test or monitoring current, and when one of these limits is passed, a signal is displayed and/or the high frequency generator is automatically shut-off. The applicable industrial standard, DIN IEC 601, Part 2—2 does not specifically require dual electrodes or monitoring circuits, but requires neutral electrodes of relatively large surface for application to the patient's body in order to provide a return path for the high frequency current at so low a level of current density that physical effects such as undesired burning are avoided. The neutral electrode is required to be applied with its entire surface reliably bearing against the body of the patient. This requirement is backed-up by official rules for high frequency surgical devices in DIN 57 753 Part I, by which attention is required to assure secure provision of contact of the neutral electrode during the entire duration of the application of high frequency current.

The practical use of the monitoring device of the above-mentioned German patent application involves several problems. As a result of more or less individual differences in the nature of the skin of the patient, the electrical resistances to be monitored vary a great deal from patient to patient, so that only insufficiently safe conclusions can be made, from the measured resistance, regarding the effectiveness of the contact surface between patient and neutral electrode. In the case of patients with dry skin the electrical contact resistance is usually remarkably greater than is the case with patients with moist skin. Furthermore, there are today many types of neutral electrodes, for example conductive or capacitive and of different surface materials such as electrically conductive plastic, gelated or dry electrodes, etc. Here again different resistance values appear, so that the equipment according to a PA 15 70 21-24 bl must be separately calibrated for each type.

The problem of the differences in the nature of the skin among various patients is intended to be dealt with by German patent DE 32 39 640 C2 disclosing a monitoring equipment which contains an adaptor unit which controls the setting of the upper and lower limits of the resistance to be measured, so that the upper limit of the electrical signal is set to depend upon the particular value of the normal electrical signal in the particular case. The system is then adapted to monitor changes of the impedance between the two electrode elements during the course of a particular treatment.

These monitoring devices have the disadvantage that the provision of sufficient safety with regard to the application of the neutral electrode to the patient depends upon how well the neutral electrode was applied to the patient before the measurement of the initial value of the impedance between the two mutually insulated electrode elements. If the neutral electrode is applied deficiently to the patient so that one or both electrode elements is or are only partly in electrically conducting contact with the skin of the patient, the upper and lower limits of the impedance would be determined from this defective initial impedance value. In addition, this equipment does not take into account the above-mentioned multiplicity of types of neutral electrodes available on the present market, so that here again the particular type of neutral electrode comes into the question as well as the characteristics of the skin of the patient.

SUMMARY OF THE INVENTION

It is an object of the present invention to develop equipment which monitors the application of neutral electrodes to the patient during high-frequency surgery in such a way that warning signals and/or shut-down of the high frequency generator will be provided when and only when the risk of thermal damage to the skin of the patient is present in the region of the contact surfaces of the neutral electrode.

Briefly, in a first embodiment a first electrical signal dependent upon the magnitude of high-frequency current flowing between the active electrode and the neutral electrode surfaces is produced and also a second electrical signal dependent upon the electrical conductivity of a current path between independent neutral electrode surfaces, as a measure of the transition resistances between the neutral electrode surfaces and the patient's body. These two signals are compared to produce at least one control signal for controlling an optical signal, an acoustic signal or interruption of the high-frequency current in response, individually, to at least one of the following eventualities: first, when the second signal is greater than the first signal; second, when the first signal is equal to or greater than the second and, third, when the first signal very greatly exceeds the second according to some predetermined criterion.

In a second embodiment the first signal is produced by an evaluation circuit dependent upon the value of a reference electrical signal representing either a reference value of the operating voltage of the high frequency electric current generator or of a desired output power of the high frequency generator, this reference electrical signal being adjustable to suit the particular occasion if desired. Again, the first signal is compared with the above-mentioned second signal to produce at least one control signal for producing an optical signal, an acoustic signal or a shut-down of high frequency current in response to the eventualities mentioned above.

It is particularly advantageous in the first embodiment to produce the first electrical signal by a thermoelectric converter, in which the high frequency current heats up a resistance, the temperature of which is used to produce the first electrical signal.

The invention has the advantage that the heating up of electrically conducting materials by electric current——and this—applies also to biological tissue—is dependent upon the electrical resistance of the material, the duration of current flow and especially on the intensity of the electric current (which has a thermal effect depending upon the square of its intensity).

In order to assure that, even at high intensities and long current flow intervals, the skin of patients in the region of the application of the neutral electrodes will not suffer thermal damage, it is evident that neutral electrodes with the greatest possible contact surfaces should be used in order to obtain the least possible electrical resistance. Upon closer consideration, however, various problems are involved in this regard. What is relevant regarding the thermal stress on the skin of patients is not the contact surface available on a neutral electrode, but its contact surface which can effectively be brought into contact with the skin of the patient. Since the surface of patients is not usually flat, but usually has concave, convex or conical shapes, as a rule only a part of the contact surface a neutral electrode that is available can be effectively brought into contact with the skin of the patient.

In addition it is known that the current distribution over the contact surface of a neutral electrode is as a rule not homogeneous. The larger the contact surface of a neutral electrode is, the greater usually is the inhomogeneity of the current density over the contact surface. It has been found that the current density is greatest within the surface portions of a neutral electrode which are closest to the active electrode.

Large neutral electrodes including their packing are more costly in their manufacturing and preparation than smaller neutral electrodes. This applies particularly to neutral electrodes designed for a single use only.

Since high current intensities are used relatively seldom and, when used, are then applied for relatively short time intervals, in the majority of all operations neutral electrodes of relatively small surface can be used. In order to assure, however, that high current intensities over longer current flow intervals do not lead to thermal damage of the skin of patients in the region where the neutral electrodes are applied, it is desirable for warning signals or automatic switchoff of the high frequency generator to be provided not only on the basis of the magnitude of the contact resistance between the neutral electrode and patient, but also from the magnitude of the high frequency current flowing through neutral or active electrodes or to be expected from the setting of the current value at the electrosurgery device, as well as the current flow duration.

The equipment according to the invention for monitoring the application of neutral electrodes to the patient during high frequency surgery accordingly consists in principle of a device which determines the transition resistance or the transition conductivity between neutral electrode and patient in some conventional way, another device which in some conventional way determines the power or voltage setting of the high frequency generator or the intensity of the high frequency alternating current flowing during high frequency surgery and then a correlation of these two parameters in such a way that a certain maximum permissible high frequency current corresponds to a certain transition conductivity so that a certain minimum permissible transition conductivity corresponds to a certain value of high frequency current and that only upon the occurrence of one of these criteria are warning signals generated or the high frequency generator automatically shut-off.

By the correlation of the transition conductivity between neutral electrode and patient on the one hand and the high frequency current that flows or is to be expected, on the other hand, various circumstances and boundary conditions are to be taken into account. If the transition resistance or the transition conductivity between neutral electrode and patient is measured by a test or monitoring current that flows between at least two neutral electrodes applied to the patient, as in the above-mentioned German patent application, such a measurement represents the series circuit of the transition conductivities from each neutral electrode to the patient, whereas the transition conductivity relevant to the heating of the skin of the patient represents only a part of the series conductivity value thus obtained. For this reason, the transition conductivity measured in accordance with the above-identified German Patent application needs to be more or less corrected. Of course the monitoring current measures the conductivity or resistance of the entire path between the neutral electrode elements, but only the transition conductivities or resistances at the contact zones of the electrodes are significant, the rest of the path having only a negligible contribution to the measurement.

Since the test current for determining the transition conductivity is not homogeneously distributed over the contact surfaces of the neutral electrodes, it is desirable according to the type and nature of the neutral electrodes to take into account a more or less strong correction of the measured transition conductivity, depending on the type and nature of the neutral electrode which is used.

In the implementation of the apparatus of the invention it is immaterial, so far as the fulfillment of the object of the invention is concerned, whether the determination of the relevant transition conductivity and of the relevant high frequency current take place simultaneously or at different times. Since the high frequency current flowing through the active and/or the neutral electrode for high frequency surgery is in general much greater than the test current flowing for the measurement of the transition conductivity at the neutral electrodes, it is, however, practical in view of the possible interfering effect of the high frequency current, to avoid measuring the transition conductivity during the intervals in which the high frequency generator is activated, and to do it instead during the pauses between activations.

In a preferred embodiment of the apparatus of the invention, the transition conductivity between neutral electrodes and patient is measured during the activation pauses of the high frequency generator and then the measurement value is transferred at each activation and stored during each activation interval (in a sample-and-hold circuit) and compared or otherwise correlated with the high frequency current either specified by the setting of the high frequency surgery device or measured during the activation of the device, —for providing optical and/or acoustic signals or automatically shutting off the high frequency generator if, or as soon as, the high frequency current is greater than the maximum permissible for the measured path conductivity.

Since high frequency currents in high frequency surgery are usually activated for very brief periods, and, moreover, their intensity fluctuates strongly during cutting and/or coagulation procedures and, moreover, are already modulated in amplitude in the high frequency generator, it is therefore useful to estimate the high frequency current before it is supplied for correlation with the measure of transition conductivity. In an embodiment of the apparatus of the invention, therefore, instead of the high frequency current flowing at the particular instant, a suitable averaging of the high frequency current is produced so that transient peak currents do not lead to false alarms or unnecessary shutting off of the high frequency generator.

The advantage of the apparatus of the invention compared to the above mentioned known systems is that warning signals and/or shutting-off of the high frequency generator during high frequency surgery take place when and only when the high frequency current is too great, or could become too great, relative to the electrical transition conductivity then present between neutral electrode and patient. As a result operations in which relatively small high frequency currents and/or only short period switchings on of high frequency current take place can be carried on without false alarms so long as the transition conductivity present at the time between neutral electrodes and the skin of the patient is not too small relative to the high frequency current. In this way even the use of smaller neutral electrodes which are fully sufficient for small high frequency currents is quite safe. If, for whatever reason, the high frequency current becomes greater than is permissible for a small neutral electrode, the apparatus of the invention generates warning signals and/or shuts off the high frequency generator. Smaller neutral electrodes are more applicable to the patient's body and are cheaper, and also easier to dispose of, than large neutral electrodes.

BRIEF DESCRIPTION OF THE DRAWINGS

The invention is further described by way of illustrative example with reference to the annexed drawings, in which.

DESCRIPTION OF THE ILLUSTRATED EMBODIMENTS

Figure 1:
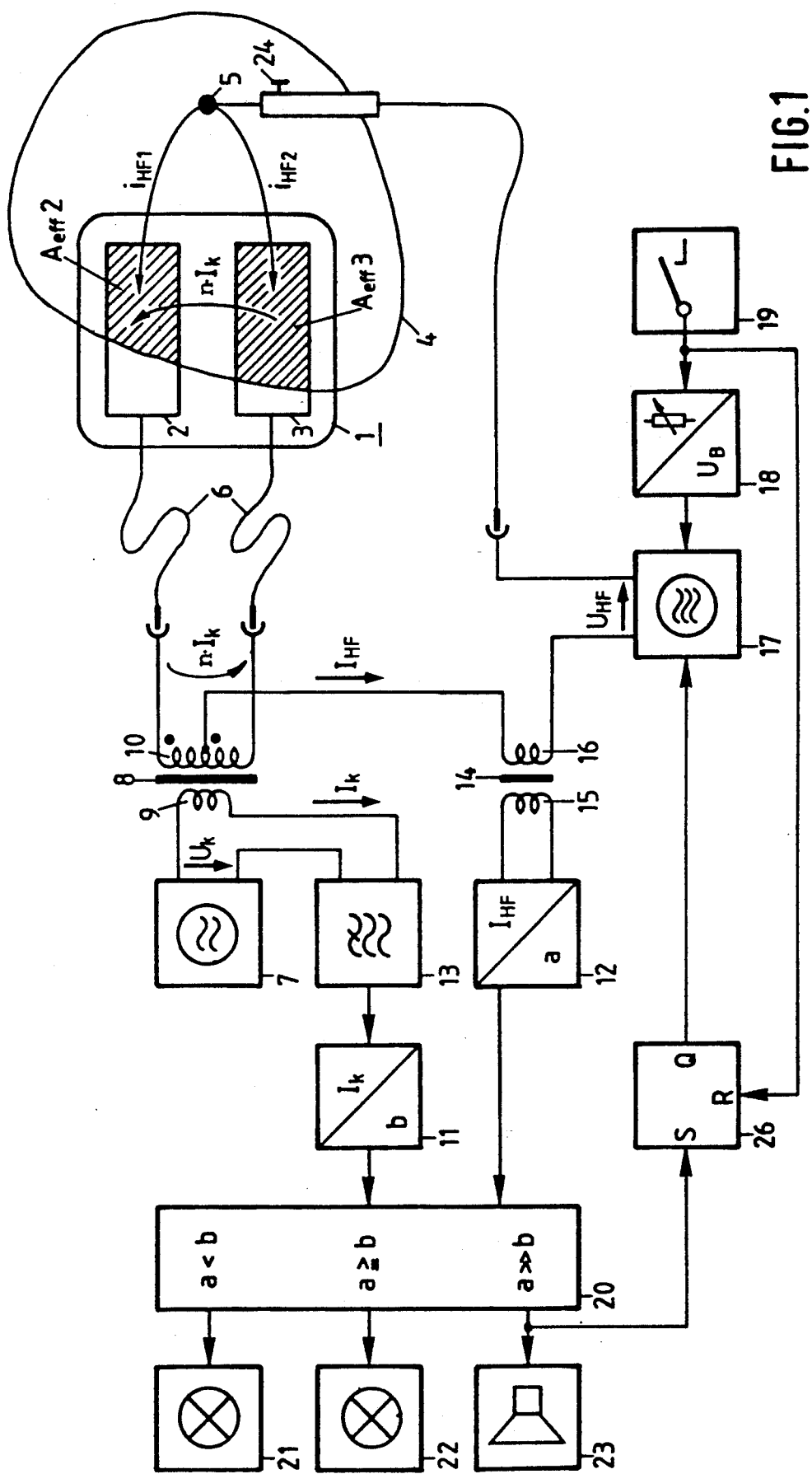
FIG. 1 is a circuit block diagram of an embodiment of the apparatus of the invention.

The principle of the equipment of the invention for monitoring the application of neutral electrodes in high frequency electro-surgery can now be described with reference to FIG. 1. It is a necessary assumption for the monitoring of the application of neutral electrodes to patients during high frequency surgery that there are either at least two neutral electrodes 2, 3 independent of each other which are applied at the same time to the same patient for or else at a neutral electrode 1 has at least two contact surfaces 2, 3, electrically insulated from each other connected over cable 6 having at least two conductors to the high frequency surgery equipment.

The transition conductivity between the contact surfaces 2, 3 of the neutral electrode 1 and the skin of the patient 4 is measured by means of a monitoring current $I_k$ in a conventional way. For this purpose a medium frequency alternating current generator 7 is provided as the voltage source which is connected through a transformer 8 and a two-wire cable 6 to the contact surfaces 2, 3 of the neutral electrode 1. When the output voltage $U_k$ of the alternating current generator 7 is constant, the monitoring current $I_k$ on the primary side of the transformer 8 or $n \cdot I_k$ on the secondary side 10 of the transformer 8 (where n is the transformation ratio of the transformer 8) is proportional to the path conductivity between the contact surfaces 2,3 and the skin of the patient 4.

As is shown in the drawing by two dots, the winding 10 of the transformer 8 is so provided that the magnetic fields which are induced by the partial currents $I_{HF1}$ and $I_{HF2}$ in the winding are equal and opposite.

When capacitive neutral electrodes are used, it is desirable for the frequency of the monitoring current $I_k$ to be equal to the frequency of the high frequency current $I_{HF}$.

An electrical signal b which is dependent upon the monitoring current $I_k$ is developed in a current sensor 11.

The high frequency current $I_{HF}$ for cutting and/or coagulating body tissues is connected to a center tap of the secondary winding 10 of the transformer 8 so that it reaches the two contact surfaces 2, 3 of the neutral electrode 1 with the most possible symmetry. The intensity of the high frequency current $I_{HF}$ is mainly dependent upon the output voltage $U_{HF}$ of the high frequency generator 17, as well as the electrical conductivity of the path between the active electrode 5 and the neutral electrode 1.

The amount (intensity) of the high frequency current $I_{HF}$ is measured and converted into an electric signal dependent upon the measured current by a current sensor 12 which for reasons of safety is isolated from the patient by means of an isolation transformer 14.

Figure 2:
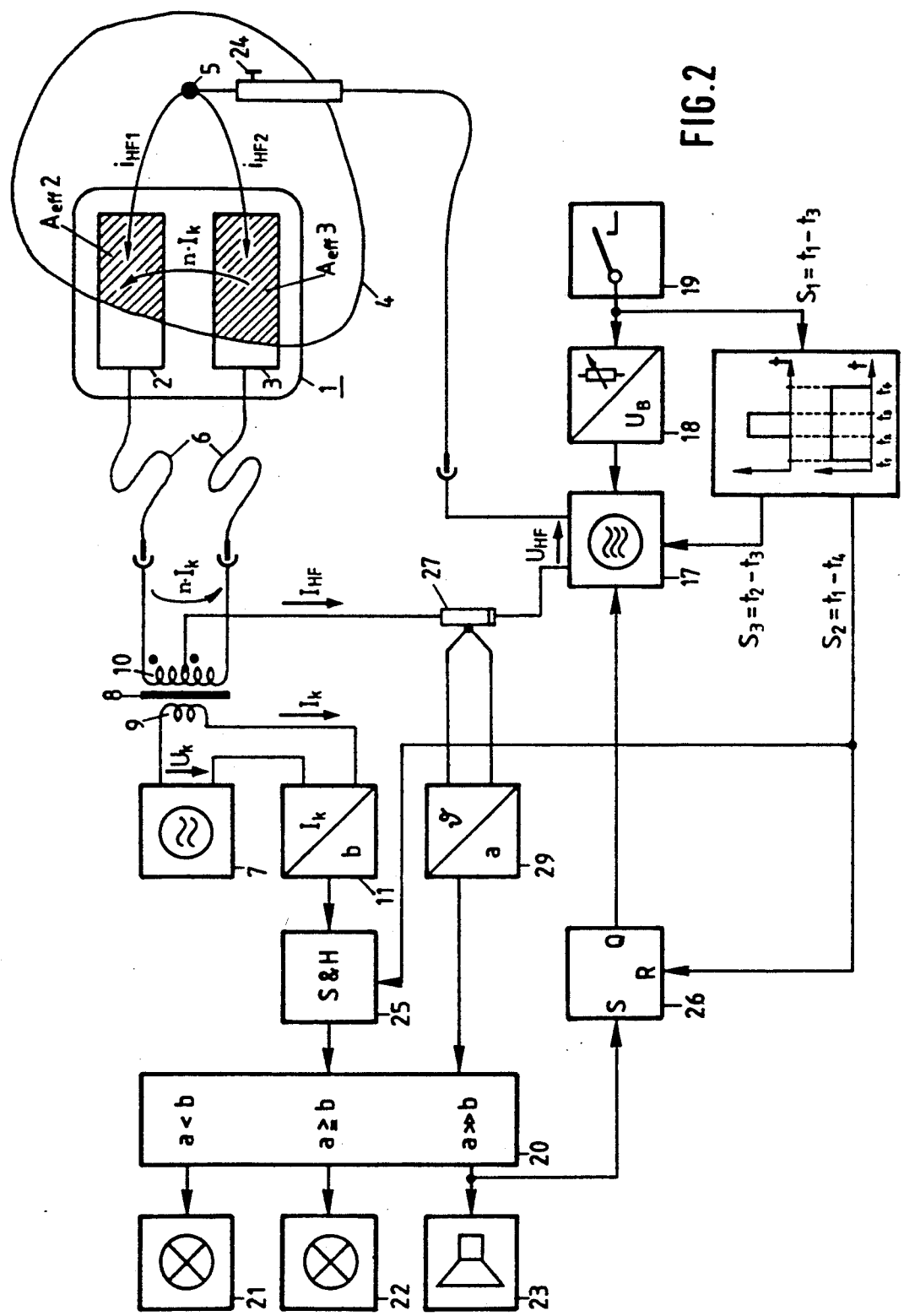
FIG. 2 is a block circuit diagram of a modification of the embodiment of FIG. 1.
Figure 3:
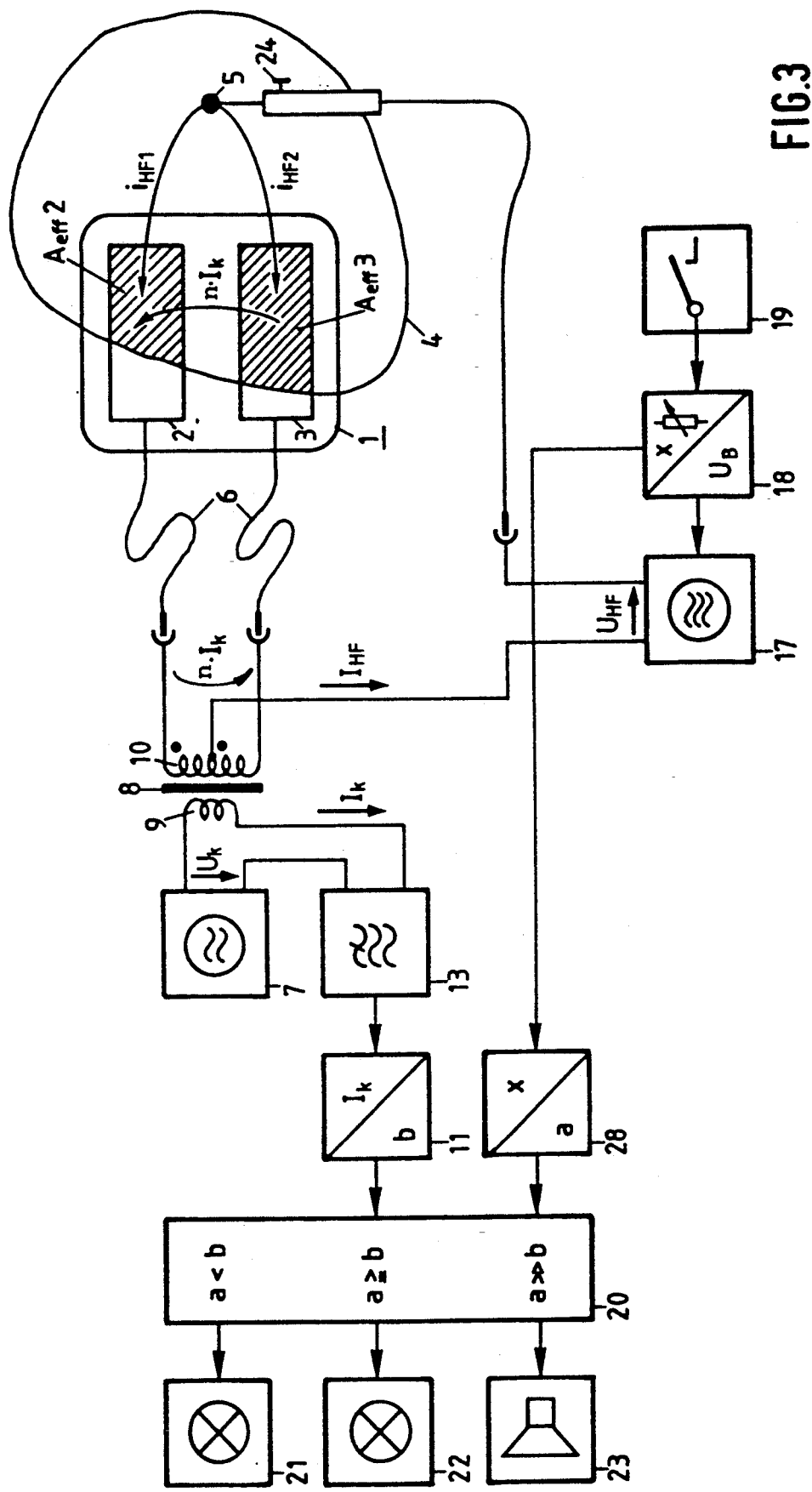
FIG. 3 is a circuit block diagram of a second embodiment of the apparatus of the invention.

Since the electrical transition conductivity between the contact surfaces 2, 3 is dependent not only from the effective contact surfaces shown shaded in FIGS. 1-3, but also from the geometry, from the spacing of the two contact surfaces 2, 3 from each other etc., it can be advantageous or even necessary for the dependence of the signal b upon $I_k$ to be corrected by a suitable function. The term effective contact surfaces signifies the portion of the available contact surface which comes conductively into contact with the skin of a patient.

The desirability or necessity of a correction proves also for the circumstance that the intensity of the monitoring current $I_k$ depends upon the series connection of the transition conductivities between the effective contact surfaces Aeff2 and Aeff3 shown shaded in FIGS. 1 to 3 and the skin of the patient, whereas the thermal loading of the skin by the high frequency current $I_{HF}$ depends on the conductivity produced by the parallel connection of these two transition conductivities.

The ratio between the transition conductivity which the monitoring current $I_k$ shows and the transition conductivity which the high frequency current $I_{HF}$ shows at the neutral electrode is dependent upon the construction of the neutral electrode that is used and can be measured in a simple way by known procedures for every type of neutral electrode and can be taken into account as a typical correction factor.

The foregoing applies also to the signal a that depends upon the high frequency current $I_{HF}$. Since the high frequency current in high frequency electro-surgery flow through the patient only for very short durations and, moreover, its intensity during cutting and coagulation procedures fluctuates strongly and is already more or less strongly modulated in amplitude in the high frequency generator and, furthermore, the heating of the biological tissue depends also on the current flow duration, it is particularly useful to use a thermo-electric converter for obtaining the signal a which is dependent upon the effective value of the high frequency current $I_{HF}$, as is illustrated, for example, in FIG. 2. For this purpose it is sufficient to let the current $I_{HF}$ flow through an ohmic resistance 27 having a suitable capacity which is large enough for the resistance on the one hand to become sufficiently warm and on the other hand to not become hot enough to overload the converter 29, while the signal a is obtained from the temperature of the resistance 27 by means of the thermo-electric converter 29. The resistance to heat flow to its surroundings from this resistance 27 can be so determined by its construction that its cooling during the pauses corresponds roughly to the cooling of the skin in its region of contact with the neutral electrode, for the heat arising in the skin of the patient as a result of the current $I_{HF}$ at the contact locations of the neutral electrode is dissipated by heat conduction and by the circulation of the patient's blood.

The generation and correction of the signals b and/or a in a manner dependent respectively on $I_k$ and $I_{HF}$ can also be carried out by a digital method wherein, for example, microprocessor circuits may be used with which in a known way any particular dependence of the signal b upon $I_k$ and/or any dependence of the signal a upon $I_{hf}$ can be implemented.

When a relatively large high frequency current $I_{HF}$ and a relatively small monitoring current $I_k$ flow simultaneously through the secondary winding 10 of the transformer 8, the evaluation of the monitoring current $I_k$ can be disturbed if the current $I_{HF}$ is not distributed itself evenly between the two contact surfaces 2 and 3 of the neutral electrode 1, i.e. when $i_{HF1}$ is smaller or greater than $i_{HF2}$.

For this reason, as shown in FIG. 1, a filter 13 is useful or even necessary to suppress any disturbance of the evaluation of $I_k$ by a difference between the high frequency partial currents $I_{HF1}$ and $i_{HF2}$. This filter and the primary circuit of the transformer 8 blocks currents with the frequency of the high frequency generator 13.

Since the high frequency current $I_{HF}$ on the one hand is present only for brief intervals during the cutting and/or coagulation procedures and on the other hand the risk that the juxtaposition of a neutral electrode might substantially deteriorate during these short interval events is negligibly small, the value of the signal b which is present before the activation of the high frequency generator 17, as shown in FIG. 2, is stored by means of a sample and hold circuit 25 during every activation period $t_2-t_3$ of the high frequency generator 17. In this connection it is advantageous to have timewise control of the activation of the high frequency generator 17 and of the sample-and-hold circuit 25 such that the activation intervals $t_2-t_3$ will always lie within the hold intervals $t_1-t_4$ of the sample-and-hold circuit.

The electrical signals a and b are supplied to a comparator 20 which compares them with each other and according to their ratio to each other generates control signals the application of which can be defined as may be useful or desirable. Thus for example a green optical signal 21 can be provided while a<b, a red optical signal 22 can be provided when a>b and/or an acoustic signal 23 can be activated, with or without the high frequency generator 17 being simultaneously deactivated, whenever a>>b according to some suitable ratio or difference threshold. When the high frequency generator 17 is automatically deactivated, it should remain deactivated until the activation switch 19 is again closed, thereby resetting an RS flip-flop 26. The deactivation can take place directly in the high frequency generator 17 or alternatively in the power supply 18.

The activation switch 19 can be a finger switch operable by the button 24 or the active electrode 5, a foot switch operable by a pedal or an automatically operated relay contact.

FIG. 3 shows another way of dealing with the problem to which the present invention is directed. It differs from the systems shown respectively in FIGS. 1 and 2 and that the signal a is not actually derived from the high frequency current $I_{HF}$ flowing through the patient, but rather from a parameter x, which is representative of, or relevant to the heating of the biological tissue and is set at the high frequency electro-surgery equipment, for example with its power supply 18. In this regard x can be the output voltage $U_{HF}$ of the high frequency generator 17, the output current $I_{HF}$ or the output power $P_{HF}$ of the high frequency generator 17.

The dependence of the signal a upon the parameter x can be defined and/or corrected in an evaluation circuit 28 which can be implemented, for example, by means of a microprocessor as already been mentioned in connection with FIGS. 1 and 2.

All other characteristics in the embodiment of FIG. 3 correspond to those embodiments shown in FIGS. 1 and 2 and described with reference thereto.

Although the invention has been illustrated with reference to particular illustrative examples, it will be understood that modifications and variations are possible within the inventive concept.

We claim:

1. Apparatus for monitoring the application, to a patient, of neutral electrode contact surfaces during high-frequency electro-surgery performed with equipment comprising at least two neutral electrodes and an active electrode, as well as a high frequency electric current generator including a power-supply for its energization, said contact surfaces comprising respective surfaces (2, 3) of said at least two neutral electrodes which are independent of each other and insulated from each other and are applied to the same patient for returning a high frequency current ($I_{HF}$) said monitoring apparatus comprising:

means (12,14–16; 28, 29) connectable in circuit with said at least two neutral electrodes and said high frequency electric current generator for producing a first electrical signal (a) dependent upon a parameter representative of heating of biological tissue of the patient;

means (7–11, 13) connectable in circuit with said at least two neutral electrodes for producing a second electrical signal (b) dependent on the electrical conductivity of a current path between said electrode surfaces (2, 3) of said independent neutral electrodes as a measure of transition conductivities between said respective electrode surfaces and the patient's body;

means (20) connected with said first signal and second signal producing means for comparing respective magnitudes of said first and second signals (a, b) and for thereby producing at least one control signal, and means connected to said comparing means and responsive to said at least one control signal for producing an optical signal, an acoustic signal or an interruption of said high frequency current, in response, individually, to at least one of the following eventualities: said second signal (b) exceeds said first signal (a) in magnitude; said first signal (a) is equal to or greater than said second signal (b); said first signal (a) greatly exceeds said second signal (b).

2. The apparatus of claim 1 wherein said means for producing a first electrical signal are evaluation circuit means (28) for producing a first variable electrical signal (a) dependent upon the value of a reference electrical signal X representing a desired reference value of operating voltage ($U_B$) for said high frequency electric current generator and means for setting and adjusting the value of said reference signal (X) and supplying said reference signal (X) to a control portion of said power supply of said high frequency generator to a value corresponding to a desired output voltage ($U_{HF}$) of said high frequency current ($I_{HF}$) or corresponding to a desired output power ($P_{HF}$) of said high frequency electric generator.

3. The apparatus of claim 2, wherein said means responsive to said at least one control signal for producing an optical signal, an acoustic signal or an interruption of said high frequency current is equipped for providing an optical signal (21) whenever said first electrical signal (a) is of smaller magnitude than said second electrical signal (b).

4. The apparatus of claim 2, wherein said means responsive to said at least one control signal for producing an optical signal, an acoustic signal or an interruption of said high frequency current is equipped for providing an optical signal (22) whenever said first electrical signal (a) is equal to or greater than said second electrical signal (b).

5. The apparatus of claim 2, wherein said means responsive to said at least one control signal for producing an optical signal, an acoustic signal or an interruption of said high frequency current is equipped for activating an acoustic signal (23) or automatically interrupting said high frequency current by shutting down said high frequency generator (17) or both activating an acoustic signal and interrupting said high frequency current whenever said first electrical signal (a) is equal to or greater than said second electrical signal (b).

6. The apparatus of claim 2, wherein said means responsive to said at least one control signal for producing an optical signal, an acoustic signal or an interruption of said high frequency current is equipped for activating an acoustic signal (23) or automatically interrupting said high frequency current by shutting down said high frequency generator (17) or both activating an acoustic signal and interrupting said high frequency current whenever said first electrical signal (a) greatly exceeds said second electrical signal (b).

7. The apparatus of claim 2, wherein said means responsive to said at least one control signal for producing an optical signal, an acoustic signal or an interruption of said high frequency current is equipped for activating an acoustic signal (23) or automatically interrupting said high frequency current by shutting down said high frequency generator (17) or both activating an acoustic signal and interrupting said high frequency current whenever said first electrical signal (a) greatly exceeds said second electrical signal (b).

8. The apparatus of claim 2, wherein a microprocessor provided with suitable software is provided in said means for producing said second electrical signal (b) for correcting the dependence of said second electrical signal (b) from said electrical conductivity of said current path between said independent electrode surfaces or from a control current ($I_k$) related thereto by applying relevant boundary conditions.

9. The apparatus of claim 1, wherein said means for producing said first electrical signal (a) includes a thermo-electric converter (27, 29) including an ohmic resistor through which said high frequency current is passed and means thermally connected to said resistor for sensing heat and producing a corresponding electrical signal as said first electric signal (a), whereby said first electrical signal (a) depends upon the effective value of said high frequency current ($I_{HF}$), said ohmic resistor (27) having a suitable heat capacity and a defined resistance to heat transmission to its surroundings.

10. The apparatus of claim 1, wherein a circuit means (25) for signal sampling and sample holding is provided to which said second electrical signal (b) is supplied, and which is connected for continuously taking over the delivery of the said first electrical signal from said means for producing said second electrical signal during intervals during which said high frequency generator (17) is not activated, said sample and hold circuit means (25) being connected for storing said value of said second electrical signal (b) during said intervals (t1-t4) and to pass on to said comparing means (20) during said intervals the value of said second electrical signal (b) which was present before the beginning (t1) of the respective interval.

11. The apparatus of claim 1, wherein said means responsive to said at least one control signal for producing an optical signal, an acoustic signal or an interruption of said high frequency current is equipped for providing an optical signal (21) whenever said first electrical signal (a) is of smaller magnitude than said second electrical signal (b).

12. The apparatus of claim 1 wherein the first electrical signal (a) is generated by the high frequency electrical current generator in dependence on a setting or reference value of the power supply (18) for the high frequency electrical current delivered by the high frequency electrical current generator (17).

13. The apparatus of claim 1, wherein said means for producing said first electrical signal (a) are means for producing a signal dependent upon the magnitude of high frequency current flowing between said active electrode (5) and said neutral electrode surfaces.

14. The apparatus of claim 13, wherein said means responsive to said at least one control signal for producing an optical signal, an acoutic signal or an interruption of said high frequency current is equipped for providing an optical signal (22) whenever said first electrical signal (a) is equal to or greater than said second electrical signal (b).

15. The apparatus of claim 13, wherein said means responsive to said at least one control signal for producing an optical signal, an acoustic signal or an interruption of said high frequency current is equipped for activating an acoustic signal (23) or automatically interrupting said high frequency current by shutting down said high frequency generator (17) or both activating an acoustic signal and interrupting said high frequency current whenever said first electrical signal (a) is equal to or greater than said second electrical signal (b).

16. The apparatus of claim 13, wherein a microprocessor provided with suitable software is provided in said means for producing said second electrical signal (b) for correcting the dependence of said second electrical signal (b) on said electrical conductivity of said current path between said independent electrode surfaces or from a control current ($I_K$) related thereto by applying relevant boundary conditions.

17. The apparatus of claim 13, wherein a microprocessor and suitable software for said microprocessor are provided for functioning as a portion of said means for producing said first electrical signal (a) for correcting the dependence of said first electrical signal (a) upon the magnitude of said high frequency current flowing between said active electrode (5) and said neutral electrode surfaces by applying relevant boundary conditions.

* * * * *